(12) United States Patent
Brosens-Kessels et al.

(10) Patent No.: US 10,183,180 B2
(45) Date of Patent: Jan. 22, 2019

(54) SYSTEM AND METHOD FOR VISUALIZING INFORMATION IN A PROCEDURE OF PLACING SOURCES

(71) Applicant: KONINKLIJKE PHILIPS N.V., Eindhoven (NL)

(72) Inventors: Angelique Carin Johanna Maria Brosens-Kessels, Eindhoven (NL); Dirk Binnekamp, Borne (NL)

(73) Assignee: Koninklijke Philips N.V., Eindhoven (NL)

( * ) Notice: Subject to any disclaimer, the term of this patent is extended or adjusted under 35 U.S.C. 154(b) by 346 days.

(21) Appl. No.: 14/911,271

(22) PCT Filed: Aug. 29, 2014

(86) PCT No.: PCT/EP2014/068440
§ 371 (c)(1),
(2) Date: Feb. 10, 2016

(87) PCT Pub. No.: WO2015/028641
PCT Pub. Date: Mar. 5, 2015

(65) Prior Publication Data
US 2016/0184611 A1 Jun. 30, 2016

(30) Foreign Application Priority Data
Aug. 30, 2013 (EP) ..................... 13182457

(51) Int. Cl.
*A61N 5/10* (2006.01)
*A61B 34/20* (2016.01)
*A61B 18/24* (2006.01)

(52) U.S. Cl.
CPC ............ *A61N 5/1071* (2013.01); *A61B 34/20* (2016.02); *A61N 5/1001* (2013.01);
(Continued)

(58) Field of Classification Search
CPC .. A61N 5/1007–5/1027; A61N 5/103–5/1031; A61N 5/1038; A61N 5/1039; A61N 5/1071; A61N 2005/1041
See application file for complete search history.

(56) References Cited

U.S. PATENT DOCUMENTS 6,311,084 B1 10/2001 Cormack et al.
6,983,230 B2 1/2006 Baroudi
(Continued)

FOREIGN PATENT DOCUMENTS

JP 2000222507 A 8/2000

*Primary Examiner* — Thaddeus B Cox

(57) ABSTRACT

A system (100) for and a method of visualizing quality information to a person performing a procedure of temporarily or permanently placing energy provision sources in a part of a body of a living being are provided. The body comprises a volume of interest. The system (100) comprising an input (104) for receiving a treatment plan (102), a data storage (108) for storing positions (P1, P2) of previously placed energy provision sources, a sub-system (106) for determining a shape and a position of the volume of interest, a tracking system (107) for obtaining tracking information relating to a placement tool for guiding a to-be-placed energy provision source towards a specific position, a processing device (110) configured for calculating a dose-volume histogram (114) for the volume of interest, and a display device (112) for presenting the dose-volume histogram (114) to the person.

12 Claims, 4 Drawing Sheets

(52) U.S. Cl.
CPC ......... *A61N 5/1007* (2013.01); *A61N 5/1027* (2013.01); *A61B 18/24* (2013.01); *A61N 5/103* (2013.01); *A61N 2005/1041* (2013.01); *A61N 2005/1074* (2013.01)

(56) References Cited

U.S. PATENT DOCUMENTS

| | | |
|---|---|---|
| 9,033,859 B2 | 5/2015 | Fieres et al. |
| 9,125,689 B2 | 9/2015 | Mielekamp |
| 2003/0065260 A1 | 4/2003 | Cheng et al. |
| 2012/0310615 A1 | 12/2012 | Moore et al. |
| 2012/0326057 A1 | 12/2012 | Remeijer et al. |

SYSTEM AND METHOD FOR VISUALIZING INFORMATION IN A PROCEDURE OF PLACING SOURCES

CROSS-REFERENCE TO PRIOR APPLICATIONS

This application is the U.S. National Phase application under 35 U.S.C. § 371 of International Application Serial No. PCT/EP2014/068440, filed on Aug. 29, 2014, which claims the benefit of European Patent Application Serial No. 13182457.5, filed on Aug. 30, 2013. These applications are hereby incorporated by reference herein.

FIELD OF THE INVENTION

The invention relates to a system for visualizing quality information to a person performing a procedure of temporarily or permanently placing energy provision sources in a part of a body of a living being.

The invention further relates to a method of visualizing quality information to a person performing a procedure of temporarily or permanently placing energy provision sources in a part of a body of a living being.

BACKGROUND OF THE INVENTION

In brachytherapy, and especially in in vivo brachytherapy, a radiation source (being an example of an energy provision source) is placed within the body at a position within or next to a tissue requiring radiation treatment. Several forms of cancer, such as prostate cancer, are treated with brachytherapy. In these forms of treatment it is important that the radiation source is placed at a predetermined position within the body to obtain the most effective treatment of the cancerous tissue. Before starting the treatment, a treatment plan is made which defines at which positions in or near the treated organ the radiation source(s) must be placed.

Also in other forms of therapy an energy emitting source is guided through a probe, needle, trocar or, for example, a catheter into the body. In these forms of therapy it is also required to know the exact position of an energy emitting source within the body. An example of such therapeutic technique is laser induced thermal therapy wherein an optical fiber is inserted through a probe into a tumor and laser light is guided to the tip of the optical fiber.

As indicated by the presentation of Berkeley University, as available on website address http://automation-.berkeley.edu/projects/needlesteering/Brachy.swf (consulted on Aug. 29, 2013), in brachytherapy a treatment plan is made with help of software which estimates the cumulative effect of the radiation dose clouds that will be produced by each radiation source. The presentation further shows how the radiation sources are inserted into the treated organ and that, during providing the radiation sources to the tissue, ultrasound equipment is used to visualize the treated organ. The presentation also discloses that the doctor who inserts needles for placing the radiation source is guided by the ultrasound display when inserting the needles in the treated organ. Thus, based on one or more subsequent images, the doctor is able to see where the needle is within the treated organ. It is known that needle placement on basis of the above procedure does not necessarily result in an accurate placement of the radiation sources. In such procedures the person who places the radiation sources does not receive enough quality feedback which, as also presented in the presentation, results in sub-optimal results.

SUMMARY OF THE INVENTION

It is an object of the invention to provide a system which provides useful quality feedback to the person who carries out a procedure of placing energy provision sources in a body.

An aspect of the invention provides a system for visualizing quality information to a person performing a procedure of temporarily or permanently placing energy provision sources in a part of a body of a living being. Another aspect of the invention provides method of visualizing quality information to a person performing a procedure of temporarily or permanently placing energy provision sources in a part of a body of a living being and a computer program is provided. Advantageous embodiments are defined in the dependent claims.

A system for visualizing quality information to a person who performs a treatment procedure of temporarily or permanently placing energy provision sources in a part of a body of a living being according to a treatment plan in accordance with the first aspect of the invention comprises an input, a data storage, a sub-subsystem for determining a shape and a position of a volume of interest, a tracking system, a processing device and a display device. The treatment plan comprises planned positions and planned amounts of energy for the energy provision sources. The body comprises a volume of interest. The input receives the treatment plan. The data storage stores positions of previously placed energy provision sources. The tracking system obtains tracking information relating to a placement tool for guiding a to-be-placed energy provision source towards a specific position in the part of the body. The tracking information relates to a trajectory followed by the placement tool and/or a present position of the placement tool. The processing device calculates a dose-volume histogram for the volume of interest on basis of the shape and the position of the volume of interest, on basis of the positions of the previously placed energy provision sources, on basis of the tracking information and on basis of a portion of the treatment plan that has not yet been carried out, the dose-volume histogram presenting a relation between a received amount of energy by a relative portion of the volume of interest. The display device presents the quality information to the person, the presented quality information comprising the dose-volume histogram.

The above system can be used in brachytherapy. In the planning phase of brachytherapy, thus, when preparing the treatment plan, a dose-volume histogram is created which summarizes the 3D dose distribution in one or more organs of interest in graphic 2D format. Also, after placing the energy provision sources in the treated organ, a dose-volume histogram is created. More information is provided on a Wikipedia webpage, which was consulted at Aug. 29, 2013 at the address http://en.wikipedia.org/wiki/Dose-volume histogram. The dose-volume histograms are traditionally used for documentation purposes only. The outcome of the treatment is more successful when the dose-volume histogram that relates to the finally placed energy provision sources substantially matches the dose-volume histogram that has been generated on basis of a treatment plan. A physician, a radiologist, or another medically trained person, uses the dose-volume histogram that relates to the finally placed energy provision sources as a measure of quality of the performed procedure. The dose-volume histogram that relates to the treatment plan is used to estimate whether the planned treatment will be effective.

The system for visualizing quality information to a person performing a procedure of temporarily or permanently placing energy provision sources provides during the procedure of placing the energy provision sources quality feedback in the form of a dose-volume-histogram to the person who performs this procedure. This feedback allows him to make better informed decisions while inserting a placement tool. The person is able to see in the presented dose-volume histogram whether the placement tool that is currently used is at a position where the to-be-placed energy radiation source is according to plan, or is following a trajectory, which results in a too large deviations in the dose-volume histogram, or which results in a dose-volume histogram that relates to a desired treatment. More in particular, when the dose-volume histogram shows too large deviations, the person may decide to adjust the position of the placement tool, or remove the placement tool without placing the energy provision source. Thus, by providing feedback to the person in the format of a dose-volume histogram, the person immediately sees the impact of his actions on the (expected) quality of the treatment and, thus, the person is able to better place the energy provision sources such that a more effective treatment is obtained.

The treatment plan comprises planned positions for the energy provision sources. The positions may be defined in the form of an offset with respect to a reference point of the body of the living being or with respect to a reference point of the volume to be treated. The treatment plan also comprises the planned amount of energy that each one of the planned energy radiation source has to administer. Often the word (planned) dose is used for the (planned) amount of energy. The sub-system for determining a shape and a position of the volume of interest may also be capable of generating geometrical data which comprises coordinates with respect to one of the reference point.

The system for visualizing quality information to the person is designed to be used during the placement of one or more energy provision sources. More in particular, when more than one energy provision sources is to be placed, the system needs to have information about positions at which some of the more than one energy provision sources is already placed. This information is stored in the data storage such that the processing device is able to access this information when calculating the dose-volume histogram.

The tracking system for obtaining tracking information is based on known systems. There are a plurality of systems available which are able to image a portion of the body and recognize a particular volume of interest in such an image. The discussed prior art presentation also shows that, for example, ultrasound equipment may be used to image the portion of the body and image recognition techniques may be used to determine a specific volume of interest, for example, an organ. The image recognition techniques may use, for example, an atlas of the body to assist the recognition of the volume of interest in the image(s) of the body.

The processing device may be a general purpose computer hick ruins a specific computer program or dedicated hardware designed to calculate the dose-volume histogram. Known technologies may be used to calculate the dose-volume histogram. In these known technologies only the planned positions (and planned amounts of energy) are used or only the positions at which the energy provision source are placed (and planned amounts of energy) are used. A difference with respect to known technologies is however which positions for the energy provision sources are used in the calculations. For energy provision sources that had been placed previously, the positions of previously placed energy provision sources as stored in the data storage is used. For a specific energy provision sources that is to be placed by the placement tool, the tracking information is used. For the energy provision sources that have not been placed yet (and is not going to be placed by the placement tool), the planned positions of the treatment plan are used to calculate the dose-volume histogram. When calculating a dose-volume histogram the processing device may take into account he planned amounts of energy of each one of the energy provision sources. Thus, for the previously placed energy provision sources, and the to-be-place energy provision source, and for not-yet-carried-out portion of the treatment plan the planned amount of energy is used for calculating the dose-volume histogram. Thus, the calculated dose-volume histogram is as accurate as possible at the moment of time that it has been calculated, because for the net yet placed energy provision source (which are the uncertainties, i.e., information that is not yet known and not yet available) planned positions are used. For energy provision source of which the position is known: the tracking information is used, and the known position is used for previously placed energy provision sources. It is to be noted that it seems not very useful to calculate a dose-volume histogram only on basis known positions because such a dose-volume histogram only relates to the previously placed energy provision source and is, therefore, incomplete. When the dose-volume histogram is only based on previously placed energy provision sources, a person, who carries out the procedure of temporarily or permanently placing energy provision sources in a part of a body, cannot see what the expected outcome of the complete procedure is. One of the insights of the inventors is to fill in the uncertainties based on the tracking information and based on the portion of the treatment plan that has not yet been carried out such that the person obtains reliable quality information which relates to the complete procedure.

Optionally, the energy provision source is one of the following: a radiation source for emitting energy in the form of radiation, a heat source which provides heat by conduction, or a source of electrical energy which comprises two electrodes for providing electrical energy to the part of the body. For example, in specific cardiological treatments, an electrical current is provided to a tissue for ablating away a portion of the tissue. Providing heat and radiation is often also done for ablating a portion of a tissue. The provided radiation may, for example, be light, X-ray or gamma radiation. Alternatively, the energy provision source may also provide "cold", which means that the energy provision source is cooled to a relatively low temperature such that it receives energy from a tissue of the body for reducing the temperature of the energy provision source.

Optionally, the tracking system is further configured to predict a continuation-trajectory of the placement tool, the continuation-trajectory is a predicted continuation of the trajectory followed by the placement tool from the present position of the placement tool. The tracking information comprises the continuation-trajectory. In order words, based on information that is obtained by the tracking system and based on knowledge about how a followed trajectory most probably continues in the body, the continuation trajectory is predicted. This generates more information for the processing tool which allows the processing tool to more accurately calculate the dose-volume histogram which corresponds to the actual placement in progress. Consequently, the person who carries out the procedure is better able to decide about the continuation of the placement of the energy provision source to be placed by the placement tool. For example, when the placement tool is a catheter and the catheter is inserted into the body via a blood vessel, the continuation-trajectory may be predicted on basis of trajectory of the blood vessel. For example, when the placement tool is a needle, the continuation-trajectory is substantially equal to a linear extrapolation of the trajectory already followed by the placement tool, and corrections are applied when the linear extrapolation coincides with relatively stiff or solid tissues. The tracking system may cooperate with the sub-system for determining a shape and a position of the volume of interest when this system also images the trajectory followed and to be followed by the placement tool. The tracking system may also cooperate with other imaging systems which generate 2D or 3D images or visualizations of the body. The tracking system may also use previously obtained 2D or 3D images or models of the body. It is to be noted that in this optional embodiment, the calculated and presented dose-volume histogram takes into account the continuation-trajectory because this information is part of the tracking information on which the calculated dose-volume histogram is based. In an embodiment, the processing unit calculates a plurality of different dose-volume histograms, for example, one which only takes into account a sub set of the available tracking information (for example, only the current position of the placement tool), and one that takes into account more tracking information (for example, also the continuation trajectory)—the display device may be configured to present the plurality of different dose-volume histograms. The reasoning of the last embodiment of calculating and presenting the plurality of different dose-volume histograms also applies to the optional embodiment that follows hereinafter.

Optionally, the tracking system is configured to predict a predicted position where an energy provision source to-be-placed is guided to on basis of the predicted continuation of the trajectory and on basis of the treatment plan. The tracking information comprises the predicted position. Thus, the calculated dose-volume histogram takes into account the position at which the energy provision source will most probably end up. Thus, the person obtains more accurate information and is able to make better informed decisions and, as such, the energy provision sources will end up at a placed position that is more in conformity of the treatment plan, more in particular, more in conformity with a dose-volume histogram that is based on the treatment plan alone. The prediction of the predicted position is based on the treatment plan and the continuation-trajectory. This means that when the continuation-trajectory coincides with planned positions of the treatment plan, the predicted position will be one of the coinciding planned positions. It may also be that, when the continuation-trajectory does not coincide with planned positions of the treatment plan, the predicted position is a position on the continuation-trajectory close to a planned position of the treatment plan.

Optionally, the treatment plan comprises an ideal dose-volume histogram or the processing unit calculates an ideal dose-volume histogram on basis of the treatment plan and the display device is configured to present the ideal dose-volume histogram as well. Thus, the ideal dose-volume histogram relates to the situation in which all the energy provision sources are placed at the planned positions. When presenting the ideal dose-volume histogram together with the dose-volume histogram that is based on the already placed energy provision sources, the tracking information and the portion of the treatment plan, the person is able to see how much the most recently calculated dose-volume histogram deviates from the ideal situation.

Optionally, the processing device is also configured to determine a deviation bandwidth and the deviation bandwidth indicates how much a dose-volume histogram may deviate from the ideal dose-volume histogram such that the treatment will be effective. The display device also displays the deviation bandwidth together with the dose-volume histogram. It is to be noted that the deviation bandwidth indicates within which bandwidth the final dose-volume histogram relates to a high quality treatment, in other words, how the dose-volume histogram has to look like when all energy provision sources are placed. The bandwidth may be based on a predefined deviation percentage, but may also be based on knowledge obtained in clinical studies about effectiveness of specific doses in treatments with provided amounts of energy to the part of the body.

Optionally, the sub-system for determining the shape and the position of the volume of interest also determines a shape and a position of a further volume of interest. The processing device is further configured to calculate a further dose-volume histogram for the further volume of interest and the display devices displays the further dose-volume histogram together with the dose-volume histogram. When, for example, the volume of interest is an organ that must be treated, it is often important to know the dose-volume histogram of organs in the neighborhood of the treated organ. It might be important that the neighboring organs do not received too much energy to prevent permanent damage. By providing a further dose-volume histogram, the person gets more accurate information about the quality/results of the placement of the energy provision sources, and, as such, the person is capable of more accurately placing the energy provision sources to a correct position within the body.

Optionally, the dose-volume histogram and/or the further dose-volume histogram are a cumulative dose-volume histogram. Instead of presenting for each specific dose bin how which relative part of the volume of interest receives this amount of dose, consecutive bins are cumulated to obtain a specific sub-class of dose-volume histograms that presents which relative part of the volume of interest receives at least an amount of dose of a specific dose bin.

Optionally, the system may further comprise a position determination system for determining a placed position at which the placement tool temporarily or permanently placed the energy provision source to-be-placed. The determination system is configured to provide the placed position to the data storage for storing the placed position together with other stored positions. The position determination system may be integrated with, for example, the tracking system or may be a separate system which accurately determines at which position the energy provision source is placed. The position determination system may be an imaging system which generates 2D or 3D images of portions of the body and in which, by means of pattern/object recognition technologies, the energy provision sources are recognized. The position determination system may also be a system that is directly coupled to or linked to the placement tool such that, at the moment that the placement tool actually places the energy provision source, the position can be determined very accurately.

Optionally, the placement tool is a needle for guiding the energy provision source towards the specific position. In many forms of treatment, for example in brachytherapy, needles are effective placements tools for guiding the energy provision source towards the specific position. In another embodiment, the placement tool is a hollow instrument for guiding the energy provision source through the hollow interior of the hollow instrument. The hollow instrument may be flexible, for example, the placement tool may be catheter. Other embodiments of the placement tools are trocars and probes According to a further aspect of the invention, a method of visualizing quality information to a person performing a procedure of temporarily or permanently placing energy provision sources in a part of a body of a living being is provided. The body comprises a volume of interest. The method comprises the stages of: i) receiving a treatment plan for treating the part of the body with energy provision sources, the treatment plan comprises planned positions and planned amounts of energy for the energy provision sources, ii) storing positions of previously placed energy provision sources, iii) determining a shape and a position of a volume of interest, iii) obtaining tracking information relating to a placement tool for guiding a to-be-placed energy provision source towards a specific position in the part of the body, the tracking information relates to a trajectory followed by the placement tool and/or a present position of the placement tool, iv) calculating in a processing device a dose-volume histogram for the volume of interest on basis of a determined shape and determined position of the volume of interest, on basis of the positions of the previously placed energy provision sources, on basis of the tracking information and on basis of a portion of the treatment plan that has not yet been carried out, the dose-volume histogram presenting a relation between a received amount of energy by a relative portion of the volume of interest, v) presenting the dose-volume histogram on a display device to the person.

According to another aspect of the invention, a computer program is provided which comprises instructions for causing a processor system to perform the method of the above discussed method.

Optionally, the computer program is embodied on a computer readable medium.

The method and the computer program according to the above discussed aspects of the invention provide the same benefits as the system according to the first aspect of the invention and have similar embodiments with similar effects as the corresponding embodiments of the system.

The computer program may be a computer program for a distributed processor system and may comprise computer code which causes a first processor system to perform a subset of the steps of the above discussed method and which causes a second processor system to perform another subset of the steps of the above discussed method. The subset of steps and the another subset of steps may be mutually exclusive.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful.

Modifications and variations of the system, the method, and/or of the computer program product, which correspond to the described modifications and variations of the system, can be carried out by a person skilled in the art on the basis of the present description.

Figure 1:
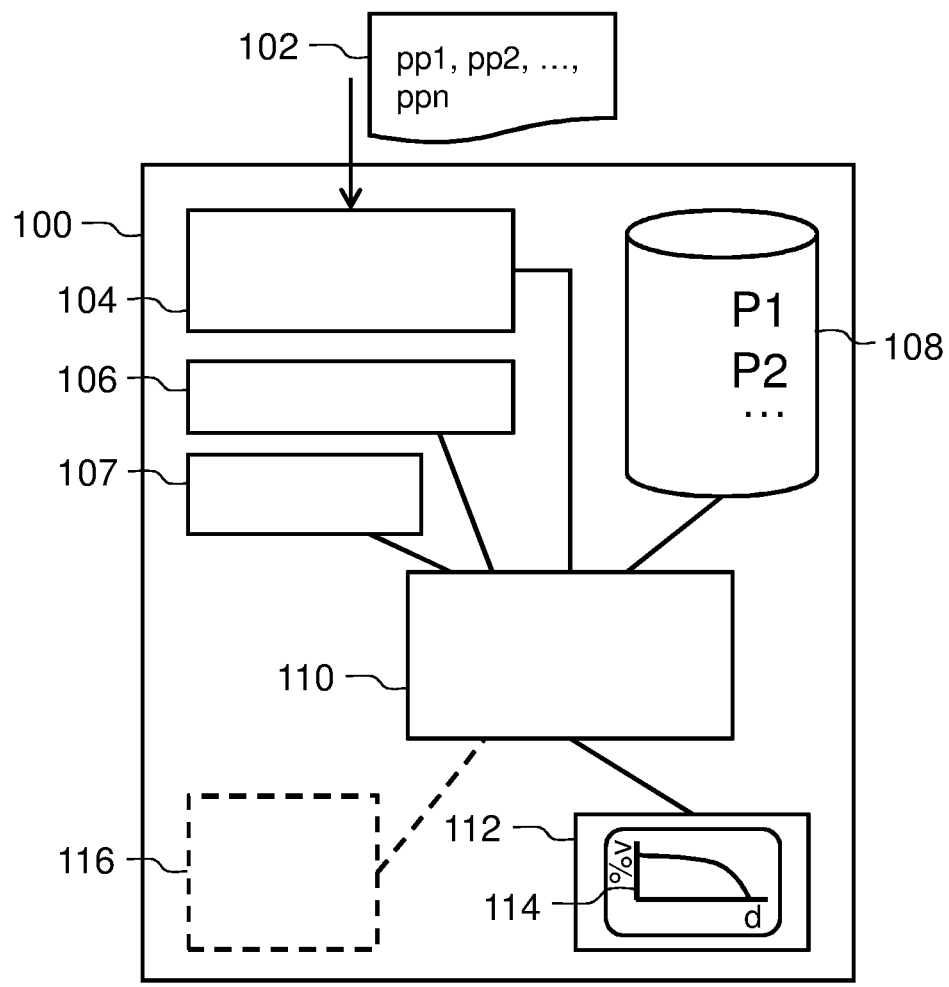
FIG. 1 schematically shows an embodiment of the system according to the invention, FIG. 2 schematically shows an organ (which is a volume of interest) in which some energy provision sources are provided, FIG. 3 schematically shows an embodiment of a cumulative dose-volume histogram, FIG. 4 schematically shows an embodiment of a method according to the invention.

It should be noted that items denoted by the same reference numerals in different Figures have the same structural features and the same functions, or are the same signals. Where the function and/or structure of such an item have been explained, there is no necessity for repeated explanation thereof in the detailed description.

The Figures are purely diagrammatic and not drawn to scale. Particularly for clarity, some dimensions are exaggerated strongly.

DETAILED DESCRIPTION OF THE EMBODIMENTS

FIG. 1 schematically shows an embodiment of a system 100 according to the invention. The system 100 is configured to assist a physician when temporarily or permanently placing energy provision sources in a part of a body of a living being. The body comprises a volume of interest, for example, a volume that must be treated. The volume of interest is, for example, an organ. In an embodiment, the living being is a human, or, in other words, a patient. In the following of this detailed description, at every location where the term "physician" is used, it has also been intended to generally refer to a medically trained person, such as a doctor, a surgeon, a radiologist and, more in general, a person who is trained to perform a procedure of temporarily or permanently placing energy radiation sources in a part of a body of a living being.

The energy provision sources that are temporarily or permanently placed may be one of the following types of energy provision sources: a radiation source for emitting energy in the form of radiation (e.g. light, X-ray or gamma radiation), a heat source, or a source of electrical energy (for example, a tool with two electrodes across which a voltage is provided such that, when the electrodes are in contact with a tissue, a current is going to flow though the tissue). In another embodiment, the energy provision source may be a cooled element which retracts heat from a tissue when it is brought in contact with the tissue. In an embodiment, the energy provision sources are configured to ablate (on the short term or medium-long term) portions of tissues/organs being present in the part of the body.

The system 100 comprises an input 104, a data storage 108, a sub-system 106 for determining a shape and a position of the volume of interest, a tracking system 107, a processing device 108 and a display device 112. The processing device 108 is coupled to the input 104, the data storage 108, the sub-system 106 and the tracking system 107 for receiving data. The processing system 108 is also coupled to the display device 110 for providing an image to be displayed to the display device 112.

The input 104 receives a treatment plan 102 for treating the part of the body with energy provision sources. The treatment plan 102 comprises planned positions pp1, pp2, . . . , ppn for the energy provision sources. The treatment plan 102 also comprises the planned amount of energy (not shown) that must be administered by the energy provision sources. It may be that all energy provision sources have to administer the same amount of energy, but it is also possible that the treatment plan prescribes that specific energy provision sources have to administer another amount of energy than other energy provision sources. Often the term "dose" is used for "the amount of energy" that must be administered. The treatment plan 102 is made before actually placing the energy provision sources. Based on a diagnosis, an expected effective treatment and previously obtained 2D or 3D images of the part of the body, the planned positions pp1, pp2, . . . , ppn are determined. The treatment plan may also comprise information about the amount of energy that is going to be provided by each individual energy provision source.

The data storage 108 is configured to store positions P1, P2, . . . of previously placed energy provision source. When no energy provision sources are placed yet, the data storage does not store such positions P1, P2, . . . . When the energy provision sources are temporarily placed, their temporarily position at which they provided the energy is stored in the data storage 108.

The sub-system 106 for determining a shape and a position of the volume of interest may be based on 2D or 3D imaging techniques for imaging portions of the body. The sub-system 106 for determining may further comprise an image processing unit which recognizes the volume of interest in the 2D or 3D images based on, for example, an atlas of the body. When the volume of interest is recognized in the images, its exact shape can be determined and its exact position within the body can be determined. It is to be noted that determining a shape and a position of a specific volume of interest may be based on known medical imaging techniques.

The tracking system 107 is configured to obtain tracking information relating to a placement tool which is used for guiding a to-be-placed energy provision source towards a specific position in the part of the body. The tracking information relates to a trajectory followed by the placement tool, for example, up to the moment that the tracking information is provided to the processing device and/or the tracking information relates to the present position of the placement tool. When placing the energy provision sources in the part of the body, the physician uses specific tools to guide the energy provision sources towards a position which is, in the ideal case, equal to one of the planned positions pp1, pp2, . . . , ppn of the treatment plan 102. The placement tool is, for example, a needle or a catheter. This may be done by obtaining 2D or 3D images of the part of the body and using image recognition techniques to recognize the placement tool in the images. Other techniques may also be used, for example, the placement tool may comprise one or more coils which register an electro-magnetic field that is present in the room in which the system 100 is in use. By analyzing the signals registered by the coils, the exact position of the placement tool may be calculated. In order to obtain tracking information that relates to the trajectory followed, the tracking system may comprise recording facilities for recording consecutive positions of the placement tool in the body. In an optional embodiment of the tacking system 107, the tracking system 107 is also configured to predict a continuation-trajectory of the placement tool. The continuation-trajectory is a predicted continuation of the trajectory followed by the placement tool and the continuation-trajectory starts from the present position of the placement tool. In addition to previously discussed type of information of tracking information, the continuation-trajectory is also added to the tracking information and, as such, used by the processing device. In an embodiment, the prediction of the continuation trajectory is based on extrapolating the trajectory followed up to the moment that the continuation trajectory is predicted. Thus, for example, a curve is fitted to the trajectory followed up to the moment that the continuation trajectory is predicted and this cure is used in the extrapolation. In a further embodiment, the tracking system is also configured to predict a predicted position where the to-be-place energy provision source is guide to on basis of the predicted continuation-trajectory and on basis of the treatment plan 102. The predicted position is the position at which the to-be-placed energy provision source is most probably going to end up within the part of the body. In an embodiment, the predicted position is a point on the predicted continuation trajectory at a predetermined z-coordinate that corresponds to the z-coordinate of the planned position of the to-be-placed energy provision source. In this embodiment it is assumed that the z-dimension is the dimension that corresponds to an ideal linear placement trajectory to reach the planned position of the to-be-placed energy provision source. The z-dimension relates to one of the few parameters which the physician is able to manipulate, namely, the length along which the placement tool is inserted into the body. The predicted position will also be added to the tracking information and as such it might be used by the processing device.

The processing device 110 receives from thee input 104 the treatment plan 102, receives from the data storage 108 positions P1, P2, . . . of previously placed energy provision sources, receives from the system 106 the shape and the position of the volume of interest and receives from the tracking system 107 the tracking information. The processing system 110 calculates a dose-volume histogram for the volume of interest on basis of the determined shape and the (determined) shape and the (determined) position of the volume of interest, on basis of the positions P1, P2, . . . of previously placed energy radiation sources, on basis of the tracking information and on basis of a portion of the treatment plan 102 that has not yet been carried out. The dose-volume histogram presents a relation between a received amount of energy by a relative portion of the volume of interest. A sub-class of dose-volume histograms is a cumulative dose-volume histogram which presents which relative portion of the volume of interest receives at least which amount of dose. It is known how to calculate dose-volume histograms and, in the context of this document, the positions of the energy provision sources that are used to calculate the dose-volume histogram is unique. Some information is known which high certainty, namely the position of the previously placed energy provision sources. Furthermore, for the to-be-placed energy provision source, relatively certain information is available which indicates where the to-be-placed energy provision source is going to be placed—this relatively certain information is the tracking information. Subsequently, for energy provision sources that are not yet placed it is not exactly known where they are going to end up in the part of the body, but a relatively good indication are the planned position pp1, pp2, . . . , ppn of the treatment plan 102. Thus, the calculated dose-volume histogram presents the dose-volume histogram that best presents the actual situation of the placement of energy provision sources. In other words, based on the calculated dose-volume histogram, the physician is best able to determine how the dose-volume histogram is going to look like if all energy provision sources that are not yet placed are exactly placed at their planned positions. It is to be noted that the processing device also takes into account the amount of energy that is provided or is going to be provided by the individual energy provision source. The information about the amount of energy may be present in the treatment plan 102, and may, for already placed energy provision sources, be based on measurements in relation to the amount of energy provided by the already placed energy provision sources.

The display device 112 is coupled to the processing device 110 and receives graphical information in relation to the calculated dose-volume histogram. The display device 112 presents the calculated dose-volume histogram 114.

The system 100 is, in particular, suitable for continuous use during the complete procedure of placing a plurality of energy provision sources in the part of the body. This means that a plurality of consecutive dose-volume histograms are determined. And, also expressed in other words, the dose-volume histogram is dynamically updated. The processing device 110 may be configured to generate, after generating a first dose-volume histogram, updated dose-volume histograms which are based on a previously calculated dose-volume histogram and which is updated with respect to the previously calculated dose-volume histogram on basis of recently obtained tracking information. Calculating updated dose-volume histograms may lead to an additional efficiency in the processing device 100.

In an embodiment, the treatment plan 102 may also comprises an ideal dose-volume histogram. The ideal dose-volume histogram is the dose-volume histogram that is aimed for in order to obtain an effective treatment of the part of the body. The ideal dose-volume histogram matches with the planned positions pp1, pp2, . . . , ppn of the energy provision sources. When such an ideal dose-volume histogram is not present in the treatment plan 102, the processing device 110 may be configured to calculate the ideal dose-volume histogram on basis of the information being present in the treatment plan. When, according to this particular embodiment, the ideal dose-volume histogram is available, the display device 112 may be configured to present the ideal dose-volume histogram as well.

Optionally, the system 100 comprises a position determination system 116 which is capable of determining a placed position at which the placement tool temporarily or permanently placed the to-be-placed energy provision source. The determination system 116 is configured to provide the placed position to the data storage for storing the placed position together with the position of previously placed energy provision sources. This embodiment guarantees that the data in the data storage is updated when the to-be-placed energy provision source is placed such that, when a subsequent to-be-placed energy provision source is guided by the placement tool towards its planned position, the system 100 is able to generate the dose-volume histogram that best matches with the actual situation (of the placement process). It is to be noted that the position determination system 116 may be integrated with the tracking system 107 and that the position determination system 116 may be based on similar technologies like recognizing objects in obtained 2D or 3D images of the body.

The treatment plan 102 comprises planned positions for the energy provision sources. The positions may be defined in the form of an offset with respect to a reference point of the body of the living being or with respect to a reference point of the volume to be treated. It might be that the system 100 translates, during use, reference points to other reference, for example, to a reference point of the room in which the body is present during the placement of the energy provision sources. Input for such a translation may be provided before the placements starts by means of manual input, or on basis of measurements made by a specific measurement tool. It might be useful to translate positions of the treatment plan 102 towards position with respect of a reference point in the room because the position of other position determining devices and system (sub-system 106 for determining a shape and a position of the volume of interest and of the tracking system) is well defined with respect to such a reference point in the room. The sub-system 106 for determining a shape and a position of the volume of interest may also be capable of generating geometrical data which comprises coordinates with respect to one of the above presented references points. In general it might be useful to translate coordinates towards a references point of the volume of interest. During the placement of the energy provision source, the volume of interest may obtain a different shape or the position may slightly change, and because the dose-volume histogram is calculated for the volume of interest, in specific embodiments, positions and/or coordinates are stored and processed with respect to a reference point of the volume of interest. In an embodiment, the system 100 takes into account changes of the shape (and/or position) of the volume of interest when it has been detected that the shapes changes over time—for example, coordinates and positions are adapted with respect to the changes of the shape (and/or position).

Figure 2:
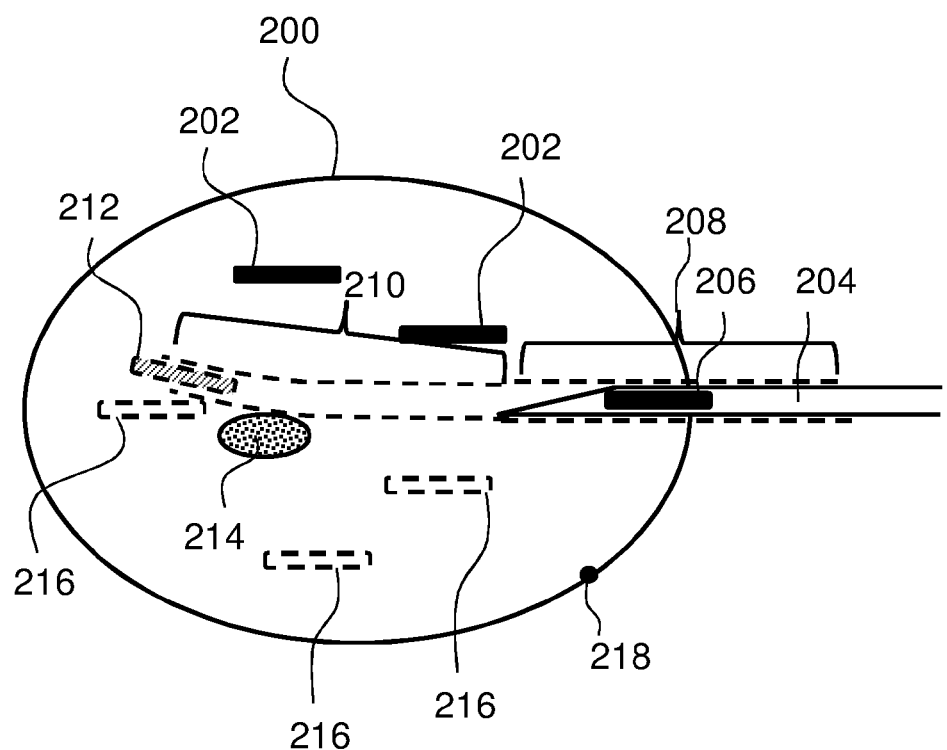

FIG. 2 schematically shows an organ 200 in which some energy provision sources 202 are already placed and in which a placement tool 204 is inserted for guiding the to-be-placed energy provision source 206 towards a planned position 216. In the embodiment of FIG. 2 the placement tool is a hollow needle 204 through which the to-be-placed energy provision source may be pushed towards a specific position within the organ. Alternatively, the placement tool 204 already comprises the to-be-placed energy provision source 206 when being inserted into the organ 200 and when the placement tool 204 reaches a position at which the to-be-placed energy provision source 206 must be placed, a release mechanism releases the to-be-placed energy provision source 206. In an example, as shown in FIG. 2, the energy provision sources 202, 206 are so-termed seeds which emit a radiation (e.g. X-ray or gamma radiation). FIG. 2 presents a situation in which already two energy provision sources 202 are placed—the system 100 of FIG. 1 stores their position in the data storage 108. In the context of FIG. 2, the system 106 determines the shape and the position of the organ 200 by means of previously discussed technologies. The information representing the shape may be represented in a specific data format, for example, a representation of a triangulated surface. The position of the organ 200 might be represented as a reference point 218 of the organ with respect to a reference point of the body or a reference point in the room in which the body is present while placing the energy provision sources. The tracking system 107 of FIG. 1 determines the trajectory followed and the current position of the placement tool 204. In FIG. 2 the trajectory followed is indicated with 208. The trajectory followed 208 is not limited to the volume of interest only (which is in the example of FIG. 2 the organ 200). The trajectory followed 208 may relate to the complete trajectory followed by the placement tool though the body, or may relate to a trajectory followed by the placemen tool through a portion of the body. The tracking system 107 of FIG. 1 may also predict a continuation-trajectory which is an extrapolation of the trajectory followed. A possible continuation-trajectory is schematically indicated with 210. When the organ 200 is a relatively soft tissue, the most logical extrapolation of the followed trajectory 206 is a linear extrapolation of the followed trajectory 206. This is also shown. The tracking system 107 of FIG. 1 may also be configured to take into account whether the organ 200 comprises also more stiff or solid tissues, such as, for example, the tissue that is schematically indicated with reference number 214. When the placement tool reaches the more stiff or solid tissue 214, the continuation trajectory 210 bends away from the more stiff or solid tissue 214. The tracking system 107 of FIG. 1 may also be configured to predict a predicted position 212 at which the to-be-placed energy provision source 206 shall probably end up. Such a predicted position 212 is most probably found on the continuation trajectory 210 and will be close to one of the planned positions 216 of the treatment plan. The predicted position 212 and/or the continuation trajectory 210 is provided as part of the tracking information to the processing device 110 of FIG. 1 and may be used by the processing device 110 to calculate the dose-volume histogram. In an embodiment, all positions discussed above are related to a reference point 218 of the organ 200. It may be predefined which point of the organ 200 is seen as the reference point 218 (and which is defined, for example, in the treatment plan), but in other embodiments this point me be interactively chosen by the physician or chosen by the system 100 of FIG. 1 without human interaction.

Figure 3:
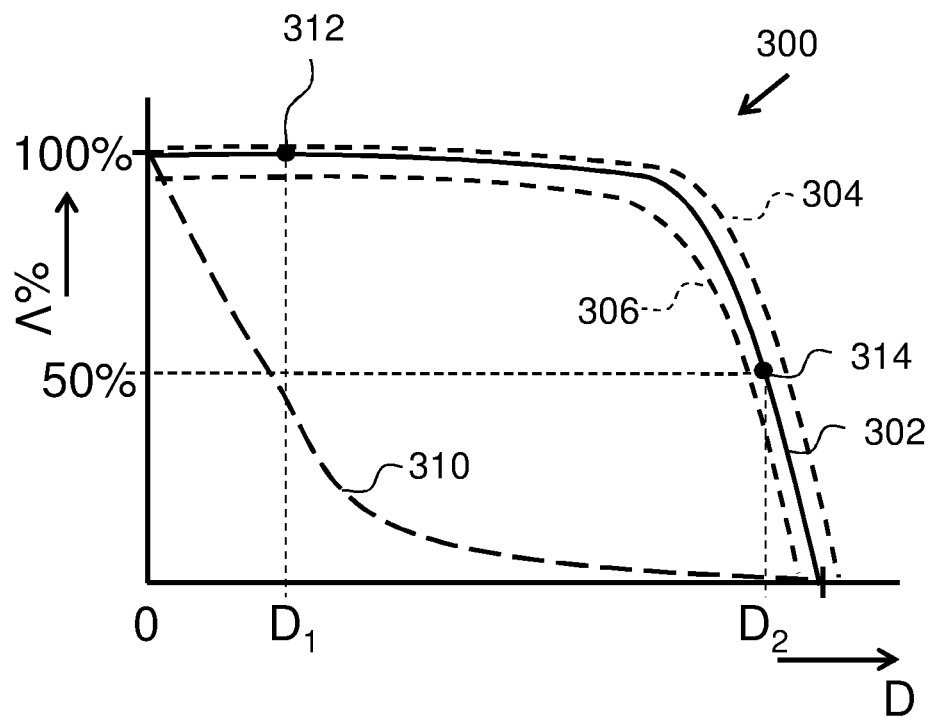

FIG. 3 schematically shows in a chart 300 an example of the above discussed dose-volume histogram 302. The chart 300 also presents an example of a further dose-volume histogram. The example of FIG. 3 presents cumulative dose-volume histograms. The dose-volume histogram 302 relates to the volume of interest. The further dose-volume histogram relates to a further volume of interest of which, in an embodiment, the sub-system 106 for determining of FIG. 1 also determines a shape and a position. The volume of interest is, for example, a treated organ and the further volume of interest is, for example, an organ or a tissue that is present at a position close to the treated organ. On the dose-volume histogram 302 a first point 312 and a second point 314 are presented to explain the information presented in a cumulative dose-volume histogram. At point 312 it has been presented at least 100% of the volume of interest at least receives the dose (an amount of energy) $D_1$. At point 314 it has been presented that 50% of the volume of interest receives at least an amount of energy (a dose) $D_2$. Thus, the dose-volume histogram 302 shows that substantially the whole volume of interest receives a relatively high dose. The further dose-volume histogram 310 shows that the further volume of interest receives only a limit amount of high doses and mainly receives relatively low doses. The chart 300 of FIG. 3 may be presented on the display device 112 of FIG. 1. It is to be noted that other dose-volume histograms may be presented together with the dose-volume histogram 302 and the further dose-volume histogram 310, such as, for example, an ideal dose-volume histogram. Even more than one ideal dose-volume histogram may be presented, for example, one for the volume of interest and one for the further volume of interest.

FIG. 3 further presents an upper limit 304 of a deviation bandwidth and a lower limit 306 of the deviation bandwidth. The processing device 110 of FIG. 1 may be configured to calculate the deviation bandwidth and the processing device 110 may provide information to the display device such that the display device is able to present information relating the deviation bandwidth (such as the upper limit 304 and the lower limit 306). Information relating to the deviation bandwidth may also be provided in the form of a bandwidth in chart 300 which has another color or which is shaded. The deviation bandwidth is a bandwidth within which the final dose-volume histogram, which is the dose-volume histogram relating to a situation in which all energy provision sources are placed, has to end up in order to have an effective treatment. Thus, as long as the dose-volume histogram, which is presented during placement of energy provision sources, is within the deviation bandwidth, the physician is informed that the placement may most probably result in a successful treatment. The processing device 110 of FIG. 1 may also calculate a further deviation bandwidth relating to the further volume of interest and the display device may present the further deviation bandwidth (not shown).

Figure 4:
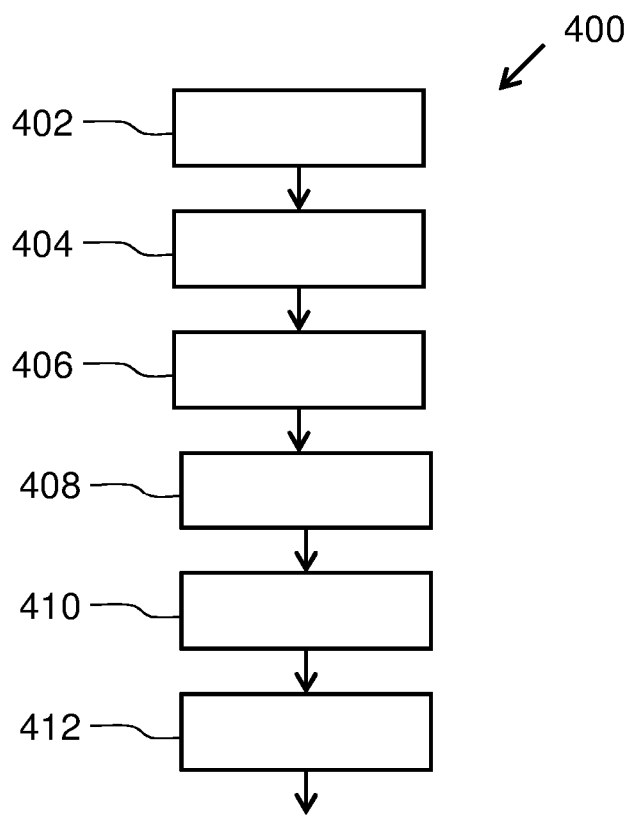

FIG. 4 schematically shows an embodiment of a method 400 according to the invention. The method 400 is a method of visualizing quality information to a person performing a procedure of temporarily or permanently placing energy provision sources in a part of a body of a living being. The body comprises a volume of interest. The method comprises the stages of i) receiving 402 a treatment plan for treating the part of the body with energy provision sources, the treatment plan comprises planned positions and planned amounts of energy for the energy provision sources, ii) storing 404 positions of previously placed energy provision sources, iii) determining 406 a shape and a position of a volume of interest, iv) obtaining 408 tracking information relating to a placement tool for guiding a to-be-placed energy provision source towards a specific position in the part of the body, the tracking information relates to a trajectory followed by the placement tool and/or a present position of the placement tool, v) calculating 410, in a processing device, a dose-volume histogram for the volume of interest on basis of a determined shape and determined position of the volume of interest, on basis of the positions of the previously placed energy provision sources, on basis of the tracking information and on basis of a portion of the treatment plan that has not yet been carried out, the dose-volume histogram presenting a relation between a received amount of energy by a relative portion of the volume of interest, and vi) presenting 412 the dose-volume histogram on a display device to the person.

It will be appreciated that the invention also extends to computer programs, particularly computer programs on or in a carrier. The computer program(s) comprise instructions for causing a processor system to perform the method 400 of FIG. 4. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

In summary, a system for and a method of visualizing quality information to a person performing a procedure of temporarily or permanently placing energy provision sources in a part of a body of a living being are provided in this application. The body comprises a volume of interest. The system comprising an input for receiving a treatment plan, a data storage for storing positions of previously placed energy provision sources, a sub-system for determining a shape and a position of the volume of interest, a tracking system for obtaining tracking information relating to a placement tool for guiding a to-be-placed energy provision source towards a specific position, a processing device configured for calculating a dose-volume histogram for the volume of interest, and a display device for presenting the dose-volume histogram to the person.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for visualizing quality information to a person who performs a treatment procedure of temporarily or permanently placing energy provision sources in a part of a body of a living being according to a treatment plan, the treatment plan comprising planned positions (pp1, pp2, ppn) and planned amounts of energy for the energy provision sources, the body comprising a volume of interest, the system comprising:
    an input for receiving the treatment plan,
    a data storage for storing positions (P1, P2) of previously placed energy provision sources,
    a sub-system for determining a shape and a position of the volume of interest,
    a tracking system for obtaining tracking information relating to a placement tool for guiding a to-be-placed energy provision source towards a specific position in the part of the body, the tracking information relating to a trajectory followed by the placement tool and/or a present position of the placement tool,
    a processing device configured for calculating a dose-volume histogram for the volume of interest on basis of the shape and the position of the volume of interest, on basis of the positions (P1, P2) of the previously placed energy provision sources, on basis of the tracking information and on basis of a portion of the treatment plan that has not yet been carried out, the dose-volume histogram presenting a relation between a received amount of energy by a relative portion of the volume of interest, and
    a display device for presenting the quality information to the person, the presented quality information comprising the dose-volume histogram.

2. A system according to claim 1, wherein the tracking system is further configured to predict a continuation-trajectory of the placement tool, the continuation-trajectory is a predicted continuation of the trajectory followed by the placement tool, the continuation-trajectory starts from the present position of the placement tool, and the tracking information comprises the continuation-trajectory.

3. A system according to claim 2, wherein the tracking system is configured to predict a predicted position where the to-be-placed energy provision source is guided to on basis of the predicted continuation-trajectory and on basis of the treatment plan, and the tracking information comprises the predicted position.

4. A system according to claim 1, wherein the treatment plan comprises an ideal dose-volume histogram or the processing device calculates an ideal dose-volume histogram on basis of the treatment plan, and the display device is configured to present the ideal dose-volume histogram as well.

5. A system according to claim 4, wherein
    the processing device is configured to determine a deviation bandwidth, the deviation bandwidth indicates how much a dose-volume histogram of a treatment may deviate from the ideal dose-volume histogram such that the treatment will be effective,
    the display device is configured to display the deviation bandwidth as well.

6. A system according to claim 1, wherein the sub-system for determining the shape and the position of the volume of interest also determines a shape and a position of a further volume of interest, wherein the processing device is further configured to calculate a further dose-volume histogram for the further volume of interest and wherein the display device is for presenting the dose-volume histogram together with the further dose-volume histogram.

7. A system according to claim 6, wherein the dose-volume histogram is a cumulative dose-volume histogram, and the further dose-volume histogram is a cumulative dose-volume histogram.

8. A system according to claim 1 further comprising a position determination system for determining a placed position at which the placement tool temporarily or permanently placed the to-be-placed energy provision source, wherein the position determination system is configured for providing the placed position to the data storage for storing the placed position together with the positions (P1, P2) of previously placed energy provision sources.

9. A system according to claim 1, wherein the energy provision source is a radiation source for emitting energy in the form of radiation, the energy provision source provides heat or cold, or the energy provision source provides electrical energy.

10. A system according to claim 1, wherein the placement tool is a needle for guiding the to-be-placed energy provision source towards the specific position.

11. Computer program comprising instructions for causing the system of claim 1 to perform, when the instructions are loaded in the system, the steps of:

receiving the treatment plan;

storing positions of previously placed energy provision sources;

determining a shape and a position of a volume of interest;

obtaining tracking information relating to a placement tool for guiding a to-be-placed energy provision source towards a specific position in the part of the body, the tracking information relates to a trajectory followed by the placement tool and/or a present position of the placement tool;

calculating in a processing device a dose-volume histogram for the volume of interest on basis of a determined shape and determined position of the volume of interest, on basis of the positions of the previously placed energy provision sources, on basis of the tracking information and on basis of a portion of the treatment plan that has not yet been carried out, the close-volume histogram presenting a relation between a received amount of energy by a relative portion of the volume of interest;

presenting quality information to the person on a display device, the quality information comprising the dose-volume histogram.

12. A computer readable medium comprising the computer program as claim in claim 11, the computer readable medium being non-transitory.

* * * * *